United States Patent [19]

Marshall et al.

[11] 4,211,763
[45] Jul. 8, 1980

[54] ANION EXCHANGE RESIN IN THE DETERMINATION OF THYROID FUNCTION

[75] Inventors: David L. Marshall, Carmel; William C. Herndon, Indianapolis, both of Ind.

[73] Assignee: The Dow Chemical Company, Midland, Mich.

[21] Appl. No.: 876,074

[22] Filed: Feb. 8, 1978

Related U.S. Application Data

[63] Continuation-in-part of Ser. No. 822,457, Aug. 8, 1977, abandoned.

[51] Int. Cl.$^2$ ............... G01N 33/16; A61K 43/00
[52] U.S. Cl. ............... 424/1; 23/230 B; 23/230.6; 252/408; 424/14; 424/19
[58] Field of Search ............... 252/408; 424/1, 14, 424/19; 260/17.4 CL, 17.4 ST; 23/230 B, 230.6

[56] References Cited

U.S. PATENT DOCUMENTS

| | | | |
|---|---|---|---|
| 3,768,979 | 10/1973 | Mead et al. | 250/303 |
| 3,938,953 | 2/1976 | Paschalis et al. | 424/1 |
| 4,015,939 | 4/1977 | Lewin et al. | 23/230 B |

OTHER PUBLICATIONS

Murphy, J. of Lab. Clin. Med., vol. 66, #1, Jul. 1965, pp. 161–167.
Sterling et al., J. Clin. Endocrin., vol. 21, Apr. 1961, pp. 456–464.

*Primary Examiner*—Benjamin R. Padgett
*Assistant Examiner*—Christine M. Nucker

[57] ABSTRACT

In the determination of thyroid function in the triiodothyronine uptake and thyroxine tests, a tablet formed from a strongly basic anion exchange resin is used as a secondary binding agent to separate the bound and unbound radioactive thyroid hormone.

3 Claims, No Drawings

ANION EXCHANGE RESIN IN THE DETERMINATION OF THYROID FUNCTION

CROSS REFERENCE TO RELATED APPLICATIONS

This application is a continuation-in-part of copending application Ser. No. 822,457 filed Aug. 8, 1977, now abandoned.

BACKGROUND OF THE INVENTION

A number of diagnostic procedures are available for evaluating thyroid function. Among the most widely used and accurate of these procedures are the diagnostic tests which measure the binding capacity of the thyroid hormone binding proteins present in a body fluid for the radioisotope labeled thyroid hormones triiodothyronine (T3) and thyroxine (T4). These are commonly referred to in the art as the T3 uptake test in the case of triiodothyronine and the T4 test in the case of thyroxine. In general, the procedures employed by the T3 uptake or T4 diagnostic tests involve the mixing of radioisotope labeled T3 (or T4) to a sample of body fluid, usually serum. Various proteins in the serum have the ability to bind the hormones. A secondary binding agent which can adsorb the hormone not already bound to the serum proteins is mixed with the serum sample. The secondary binding agent with the adsorbed hormone not originally bound to the serum protein can then be separated from the test sample. The radioactivity of either the serum sample or the secondary binding agent is measured in a suitable scintillation counter. Many variations of the general procedure have been developed; most vary in the nature of the secondary binding agent. As used herein, the term body fluid refers to a body fluid such as serum or blood which contains proteins capable of binding the thyroid hormones T3 or T4.

The secondary binding agent used to separate the unbound hormone from the test sample must have physical properties which allow it to be separated from the test solution so that the radioactivity of the separated fractions can be measured. Currently available methods use ion exchange resins in various forms (see U.S. Pat. Nos. 3,206,602; 3,714,344 and 3,414,383) or other adsorbent materials such as talc (see U.S. Pat. No. 3,666,854) and sephadex columns. Rolleri et al., *J. Nucl. Med.*, 13, 893 (1972), describes the use of water-insoluble albumin. Most of the currently available methods have the disadvantage of requiring precise timing during the test procedure. In addition, some of the methods are not convenient for handling of large numbers of tests simultaneously because of the complexity of the procedure.

SUMMARY OF THE INVENTION

The present invention is directed to a tablet useful in the measurement of the binding capacity of the protein in a body fluid which comprises a compressible strong base anion exchange resin which is able to rapidly bind the thyroid hormones T3 and T4. The tablet disintegrates rapidly, that is within 60 seconds, when in contact with the test fluid to facilitate dispersion preparatory to binding. In addition, the resin once dispersed will readily settle out once agitation is stopped and remain as a substantially adherent agglomerate at the bottom of the container so that the supernatant test fluid may be readily separated prior to measuring the radioactivity present in either the fluid or the resin. Thus the resin must have a specific gravity greater than the body fluid being tested.

The present invention is also directed to a method for binding the free thyroid hormones T3 and T4 present in a serum sample using a tabletted strong base anion exchange resin having pyridinium active ion exchange groups. The present invention is further directed to an improved method of carrying out the T3 uptake and T4 test. Thus in a method for measuring the binding capacity of the proteins in a body fluid for triiodothyronine wherein a known quantity of radioactive labeled triiodothyronine is mixed with a sample of the body fluid so as to bind to the thyroid hormone-binding-proteins in the serum sample, separating the bound and unbound radioactive triiodothyronine in different fractions by adding a secondary binding agent, and measuring the amount of radioactivity present in either or both fractions, the improvement comprises using a tabletted secondary binding agent which comprises a strong base anion exchange resin of the type herein described. Likewise, the tabletted anion exchange resins may be used in a method for measuring the amount of thyroxine in a body fluid wherein a known amount of radioactive thyroxine and thyroxine-binding-protein is mixed with a thyroxine extract from a sample of body fluid, the bound and unbound radioactive thyroxine being separated into different fractions by the addition of a secondary binding agent, and the amount of radioactivity in either or both fractions measured.

It will be understood from the above description that the present invention may be used to offer the convenience of a disintegrable tablet which is suitable as a secondary binding agent in the T3 uptake and T4 test. An additional advantage is that precise timing is not as critical when carrying out the T3 uptake and T4 test with the present invention because the resin binds substantially all of the free T3 or T4 within the normal mixing period. The resin also settles quickly once agitation is stopped so there is no adverse effect on the equilibrium established between the thyroxine and thyroxine binding globulin, hereafter called TBG, used in the T4 test.

DETAILED DESCRIPTION OF THE INVENTION

As described above, the present invention is directed to a resin tabletted form which serves as a secondary binding agent for the removal of radioactive T3 or T4 left unbound to the protein present in the fluid sample, usually serum. As used herein, the term "protein-bound hormone" refers to the hormone T3 or T4 bound to body fluid proteins present in the fluid sample prior to the addition of the secondary binding agent. The term "unbound hormone" likewise refers to the hormone T3 or T4 which remains unbound or free in the fluid sample prior to the addition of the secondary binding agent.

Anion exchange resins which are suitable for use in the present invention are powdered compressible strong base anion exchangers. They must be compatible with conventional tabletting operations, and once formed into a tablet they must be capable of rapid disintegration, that is within about 60 seconds, when in contract with the fluid sample. It is essential that when the fluid sample is not being agitated, the resin quickly settles to the bottom of the container, therefore the resin particles must not be colloidal in size. In general, resin particles of from about 50 to 400 dry mesh are suitable for use with the present invention with a dry mesh of from about 100 to 200 being preferred. Additionally, it is important that upon centrifugation, the particles form a coherent agglomeration to allow the supernatant fluid sample to be separated prior to measuring the radioactivity. The resin particles should also be of uniform particle size to assure reproducible results.

It is essential that the resin employed in the present invention have rapid binding kinetics with the thyroid hormones T3 and T4. Rapid binding kinetics means that the resin must bind at least 90% of the unbound hormone within 3 minutes following disintegration of the tablet.

The commercially available anion exchange resin Bio Rex® 9 (available from Bio Rad) has been found satisfactory for use with the present invention. Bio Rex® 9 is described as a strongly basic anion exchange resin containing pyridinium exchange groups.

The active groups on Bio Rex® 9 are represented as follows:

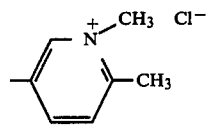

This resin is described as extremely resistant to strong oxidizing agents such as hot concentrated nitric acid.

In forming tablets using an anion exchange resin as described above, various excipients or inert materials may be mixed with the resin prior to tabletting. Such excipients may include diluents, binders, disintegrators, and lubricants. Conventional excipients which are known to the art are described in *Remington's Pharmaceutical Sciences,* 13th Ed. (Mack Publishing Co., 1965). These materials and their uses in tabletting operations are well known in the art, and the utility of such excipients in the tablet will immediately be obvious to one skilled in the art.

The following examples will further clarify the invention but are not to be considered as a limitation thereon.

EXAMPLE 1

The following illustrates one preferred formulation for a tablet used in the practice of the present invention.

| Component | Amount per Tablet |
| --- | --- |
| Bio Rex$^{(R)}$ 9 (Bio Rad) | 8 mg (dry weight) |
| Starch Powder | 12 mg (dry weight) |
| Lactose Powder | 98.4 mg (dry weight) |
| Sta Rx$^{(R)}$ (A. E. Staley) | 1.2 mg (dry weight) |
| Magnesium Stearate | 0.4 mg (dry weight) |
| Water | about 3% residual* |

*A greater amount of water is added to the mix prior to tabletting, but only about 3% remains in the finished tablet.

EXAMPLE 2

The following is a preferred method for carrying out the T3 uptake test using the present invention.

A solution is prepared containing from about 0.01 to 0.03 μCi/ml of radioactive T3 (triiodothyronine) in 0.1 M barbital, pH 8.6. A serum sample is then added to this solution. Although various serum to T3-buffer ratios can be used, a combination of 0.1 ml of serum in 2.0 ml of radioactive T3 barbital buffer produces satisfactory results. Binding between the radioactive T3 and the serum proteins occurs almost instantaneously, so the addition of the resin tablet can take place as soon as the tubes are mixed. However, a reasonable delay in addition has no adverse effects on the final result. Following the addition of the resin tablet, the tubes are capped and mixed by gentle inversion for 60 seconds. The tubes should be allowed to stand for at least five minutes and then centrifuged. The resin pellet at the bottom of each tube is counted on a suitable scintillation counter, and the counts in each test sample can be compared to the counts obtained with a known reference or control serum.

The results of the test are usually expressed as a percent uptake in which the amount of radioactive T3 in the sample tubes (bound to the ion exchange resin) is divided by the total amount of radioactive T3 present at the beginning.

EXAMPLE 3

Using the general procedure outlined in Example 2, normal and abnormal sera were tested to show the difference in percent uptake of radioactive T3. A series of measurements were made using 0.1 ml of serum sample to which 2.0 ml of radioactive T3-buffer was added. A resin tablet containing 5.6 mg of Bio Rex® 9 anion exchange resin was added to each tube and mixed for 60 seconds. After centrifuging, the pellets were counted. The results are shown in Table I below.

TABLE I

| Serum Sample | Percent Uptake |
| --- | --- |
| Normal | 29.3 |
| Hyperthyroid | 46.3 |
| Hypothyroid | 22.9 |

EXAMPLE 4

Another common diagnostic procedure for evaluating thyroid function is the measurement of serum thyroxine (T4). A popular form of assay is the thryoxine competitive binding assay in which radioactively-labeled thyroxine is added to thyroxine extracted from a serum sample, usually by alcohol extraction from coagulated serum, which results in competition between the two forms of T4 for binding sites on a protein called thyroxine binding globulin which specifically binds T4. After an incubation period, usually about 15 minutes at room temperature, the thyroxine binding globulin, hereafter TGB, is separated from the free or unbound thyroxine by adding the ion-exchange tablet to the sample, mixing for a brief period (usually about 15 to 120 seconds), and allowing the sample to stand for at least five minutes. The tubes are centrifuged, and the supernatant fluid is discarded. The tubes containing the resin pellets are counted in any suitable gamma counter. The concentration of thyroxine in the unknown sample is determined by comparison to a standard curve prepared by assaying serum thyroxine standards.

EXAMPLE 5

Using the general procedures described in Example 4 above, four standards prepared in 66% ethanol were analyzed using a 100 mg tablet containing 15 mg of Bio Rex® 9 resin. The results are shown in Table II.

TABLE II

| Thyroxine Added nanograms/tube | Counts per Minute in Pellet |
|---|---|
| 0.5 | 42662 |
| 3.0 | 49541 |
| 6.0 | 55336 |
| 9.0 | 59993 |

The results shown in Table II above may be used to construct a standard curve. Serum samples, containing unknown quantities of thyroxine may be compared to the standard curve to determine the serum thyroxine present.

What is claimed is:

1. In a method for measuring the binding capacity of the proteins in a body fluid for triiodothyronine wherein a known quantity of radioactive labeled triiodothyronine is mixed with a sample of the body fluid so as to bind to the thyroid hormone-binding-proteins in the fluid sample, separating the bound and unbound radioactive triiodothyronine in different fractions by adding a secondary binding agent, and measuring the amount of radioactivity present in either or both fractions, the improvement comprising using a tabletted secondary binding agent that contains a powdered compressible strong base anion exchange resin having pyridinium active ion exchange groups, said resin having a dry mesh size of from about 50 to 400 and being capable of binding at least 90% of the unbound triiodothyronine within three minutes following the disintegration of the tablet.

2. In a method for measuring the amount of thyroxine in a body fluid wherein a known amount of radioactive thyroxine and thyroxine-binding-protein is mixed with a thyroxine extract from as sample of body fluid, the bound and unbound radioactive thyroxine is separated into different fractions by the addition of a secondary binding agent, and the amount of radioactivity in either or both fractions is measured, the improvement comprising using a tabletted secondary binding agent that contains a powdered compressible strong base anion exchange resin having pyridinium active ion exchange groups, said resin having a dry mesh size of from about 50 to 400 and being capable of binding at least 90% of the unbound radioactive thyroxine within three minutes following the disintegration of the tablet.

3. A disintegrating tablet useful for measuring the binding capacity of the thyroid binding proteins in a body fluid which comprises a powdered compressible strong base anion exchange resin having pyridinium active ion exchange groups, the particle size of said resin having a dry mesh size of from about 50 to 400 and being capable of binding at least 90% of the unbound thyroid binding protein in the test sample within three minutes following the disintegration of the tablet.

* * * * *